United States Patent
Park et al.

(10) Patent No.: US 7,993,507 B2
(45) Date of Patent: Aug. 9, 2011

(54) SEPARATION METHOD FOR MULTI CHANNEL ELECTROPHORESIS DEVICE HAVING NO INDIVIDUAL SAMPLE WELLS

(75) Inventors: Sang-Ryoul Park, Daejeon (KR); In-Chul Yang, Daejeon (KR); Young-Ho Kim, Daegu (KR)

(73) Assignee: Korea Research Institute of Standards and Science, Daejeon (KR)

( * ) Notice: Subject to any disclaimer, the term of this patent is extended or adjusted under 35 U.S.C. 154(b) by 902 days.

(21) Appl. No.: 11/791,509

(22) PCT Filed: Nov. 16, 2005

(86) PCT No.: PCT/KR2005/003870
§ 371 (c)(1),
(2), (4) Date: Oct. 10, 2007

(87) PCT Pub. No.: WO2006/057494
PCT Pub. Date: Jun. 1, 2006

(65) Prior Publication Data
US 2008/0047834 A1 Feb. 28, 2008

(30) Foreign Application Priority Data
Nov. 26, 2004 (KR) .................. 10-2004-0097820

(51) Int. Cl.
*G01N 27/26* (2006.01)
*G01N 27/447* (2006.01)

(52) U.S. Cl. ........ 204/453; 204/601; 204/459; 204/610; 204/604; 204/451; 204/455; 204/605; 435/287.2; 435/288.5; 435/288.6; 422/68.1; 422/508; 422/507

(58) Field of Classification Search .......... 204/450–469, 204/193, 601–621; 435/287.2, 288.5, 288.6; 422/68.1, 507, 508
See application file for complete search history.

(56) References Cited

U.S. PATENT DOCUMENTS
5,628,891 A * 5/1997 Lee ............................... 204/612
(Continued)

FOREIGN PATENT DOCUMENTS
EP 1 052 504 11/2000
(Continued)

OTHER PUBLICATIONS
Seiler et al, "Planar Glass Chips for Capillary Electrophoresis: Repetitive Sample Injection, Quantitation and Separation Efficiency," Analytical Chemistry, May 15, 1993, pp. 1481-1488, vol. 65, No. 10.
(Continued)

*Primary Examiner* — Alexa D Neckel
*Assistant Examiner* — Jennifer Dieterle
(74) *Attorney, Agent, or Firm* — The Webb Law Firm

(57) ABSTRACT

The present invention is related to a method of separation of compounds by electrophoresis in which the compounds such as genes, proteins, etc. may be analyzed very precisely as samples are introduced directly into the separation tubes of the chip at the collection site, and therefore, it is not necessary to have separate fluid paths or individual sample storing apparatus that have been necessary for the conventional electrophoresis; it is easy to make the chips as the structure of the chip becomes extremely simple, and high-density arrangement of the separation tubes is enabled; and further, the compounds such as genes, proteins, etc. may be analyzed very precisely without interference in the storage tubs by using a non-polar solvent as the solvent of the sample storage tub.

5 Claims, 8 Drawing Sheets

U.S. PATENT DOCUMENTS

| | | | |
|---|---|---|---|
| 5,736,025 A * | 4/1998 | Smith et al. | 204/621 |
| 5,872,010 A | 2/1999 | Karger et al. | |
| 5,882,571 A | 3/1999 | Kaltenbach et al. | |
| 5,958,203 A * | 9/1999 | Parce et al. | 204/451 |
| 6,054,032 A | 4/2000 | Haddad et al. | |
| 6,113,762 A | 9/2000 | Karube et al. | |
| 6,364,516 B1 | 4/2002 | Li et al. | |
| 6,766,817 B2 | 7/2004 | da Silva | |
| 6,918,404 B2 | 7/2005 | Dias da Silva | |
| 7,066,586 B2 | 6/2006 | da Silva | |
| 7,242,528 B2 * | 7/2007 | Renders et al. | 359/665 |
| 7,285,255 B2 | 10/2007 | Kadlec et al. | |
| 2004/0217279 A1 | 11/2004 | Hobbs et al. | |

FOREIGN PATENT DOCUMENTS

| | | |
|---|---|---|
| EP | 1 467 202 | 10/2004 |
| KR | 1020050103028 A | 10/2005 |
| KR | 10-2004-0040408 | 12/2005 |
| WO | WO 00/26657 | 5/2000 |
| WO | WO 02/063288 | 8/2002 |
| WO | WO 2004/056697 | 7/2004 |

OTHER PUBLICATIONS

Paegel et al, "High throughout DNA sequencing with a microfabricated 96-lane capillary array electrophoresis bioprocessor," PNAS, Jan. 22, 2002, pp. 574-579, vol. 99, No. 2.

Simpson et al, "A transmission imaging spectrograph and microfabricated channel system for DNA analysis," Electrophoresis 2000, pp. 135-149, 21.

Backhouse et al, "DNA sequencing in a monolithic microchannel device," Electrophoresis 2000, pp. 150-156, 21.

* cited by examiner

Prior Art

SEPARATION METHOD FOR MULTI CHANNEL ELECTROPHORESIS DEVICE HAVING NO INDIVIDUAL SAMPLE WELLS

TECHNICAL FIELD

The present invention is related to a method of separation of compounds by electrophoresis in which the compounds such as genes, proteins, etc. may be analyzed very precisely as samples are introduced directly into the separation tubes of the chip at the collection site, and therefore, it is not necessary to have separate fluid paths or individual sample storing apparatus that have been necessary for the conventional electrophoresis; it is easy to make the chip as the structure of the chip becomes extremely simple, and high-density arrangement of the separation tubes is enabled; and further, the compounds such as genes, proteins, etc. may be analyzed very precisely without interference in the storage tubs by using a non-polar solvent as the solvent of the sample storage tub.

The present invention is related to a technology of performing electrophoresis by using a microminiaturized multi-channel electrophoresis device. The microminiaturized multi-channel electrophoresis devices have been developed as useful analytical tools enabling fast and simple electrophoresis of chemical substances, genes, proteins, etc.

As shown in FIG. 2, in the conventional electrophoresis chip, there is a separate sample injection port for the injection of a sample, and the sample is injected to a separation tube elaborately by using the cross-shaped path of the connection part between this sample injection port and the separation tube [Seiler, K. et al., Anal. Chem. 1993, 65, 1481-1488]. However, since the conventional technology of the injection of a sample using a cross-shaped fluid path for the introduction of a sample requires for a separate sample injection port and the formation of a cross-shaped path, it becomes complicated to arrange the separation tubes, and further, increasing the arrangement density of the separation tubes is limited. For this reason, in case of the DNA/RNA electrophoresis chip of Agilent Company which is on the market, there is only one separation tube per chip and 12 sample injection ports so that 12 samples are analyzed in turn by using the single separation tube. Recently, B. M. Paegel and others have published 96-channel electrophoresis chips [Paegel, P. M. et al., PNAS 2002, 99, 574-579], even in which case the structure of the chip has been designed to be radial because of individual sample injection port and cross-shaped fluid path required by each channel. The radial design not only adds the technical difficulty or non-economical aspects to manufacturing and cutting of the chip but also requires for the high-grade detection technique of operation while rotating.

In order to solve the above-described problems, multi-channel chips, from which the conventional cross-shaped fluid paths for the introduction of samples have been removed but sample storage tubs have been installed directly on separation tubes, have been published [Backhouse, J. W. et al., Electrophoresis 2000, 21, 150-156; Simpson, J. W. et al., Electrophoresis 2000, 21, 135-149]. However, even in these cases, there have been problems to be pointed out that the interval between the separation tubes has been widened since individual sample injection ports that have been relatively very larger than the separation tubes have been installed on the separation tubes, and processing of the injection tubes has been costly and difficult technically.

Therefore, proposed by the present research group is a simple-structured electrophoresis device having only one sample storage tub with individual sample storage tubs removed as shown in FIG. 1 in order to overcome the above-described problems [Korean Patent Application No. 2004-40408]. Still, in this case, when a sample is injected into one sample tub, the sample flows into other capillary tubes due to the diffusion of the sample, and thus, the accuracy of analysis is lowered as the phenomenon of electrophoresis occurs.

SUMMARY OF THE INVENTION

The present invention is to solve the above-described problems. Therefore, it is an object of the present invention to provide a method of implementing a creative sample introduction technique that is necessary for the practical use of a microminiaturized multi-channel electrophoresis device having a simple structure from which individual sample wells or cross-shaped paths are removed from the beginning.

It is another object of the present invention to provide a method of injecting samples more effectively by using a simple-structured electrophoresis device that can be manufactured at a low cost with a high-density separation tubes according to the prior application filed by the present inventors [Korean Patent Application No. 2004-40408] installed.

It is still another object of the present invention to provide an effective method and a device of separation of samples enabling the change of the lengths of chips variously as needed taking advantage of the fact that separation tubes are arranged in the form of parallel straight lines.

It is yet another object of the present invention to provide an electrophoresis device that is applicable to various types of gene analyses requiring for different separation abilities by using the chips that may be adjusted as described in the above and developing effective methods of injection.

As described in the above, the present invention is completed through electrophoresis. That is, in the present invention, in order to prevent a phenomenon of hindering the accuracy of separation caused by diffusion in a simple-structured electrophoresis device having only one sample storage tub, a non-polar solvent is inputted and stored in a sample storage tub, samples are inputted into the non-polar solvent by the corresponding sample ejection tubes, and each sample ejected to the front side of the corresponding separation tube is introduced into the corresponding separation tube by the negative electric field (or positive electric field) that is applied to the metal part of the end part of each ejection tube.

In other words, one characteristic of the present invention is to include a step of preventing diffusion by storing a non-polar solvent in a sample storage tub and inputting samples into this non-polar solvent storage tub. It is preferable to use a non-polar oil such as silicon oil, mineral oil, etc. which are viscous as the non-polar solvent used for the present invention, more preferably, silicon oil. The viscosity of the non-polar solvent to be used is not greatly limited, and therefore, can be selected and used properly.

Hereinafter, the steps of separation using a multi-channel electrophoresis device that can separate genes, proteins, etc. at a high speed according to the present invention are illustrated concretely.

(1) Structure and Installation of a Multi-Channel Electrophoresis Chip

A multi-channel electrophoresis chip may be manufactured in a method described in Korean Patent Application No. 2004-40408 filed by the prevent inventors. Briefly speaking, as shown in FIG. 1, a multi-channel electrophoresis chip (2) is manufactured by arranging a multiple number of fused silica capillary tubes having an inner diameter of 10-200 μm and an outer diameter of 300~400 μm on a plastic substrate onto which groves are formed lengthwise to have proper width and depth, and forming a sedimentation resin such as epoxy resin, urethane resin, phenol resin, silicon resin, acryl resin, etc. by filling a monomer or oligomer that may be hardened by a hardening agent. This multi-channel electrophoresis chip (2) is inserted into the lower side of an electrophoresis device (10). That is, an electrophoresis device (1) with a storage tub (3), in which a non-polar solvent is stored, and a multi-channel electrophoresis chip (2) installed is manufactured.

The multi-channel electrophoresis chip of the present invention may be manufactured by varying the length of the chip properly through cutting with a diamond-wheel saw for practical applications. Accordingly, sometimes, multi-channel electrophoresis chips having different lengths may be adopted and used according to the samples to be separated.

More concretely, in the above electrophoresis device (1), as shown in FIG. 3, an electrophoresis chip (2) with multiple capillary separation tubes (1) formed is put on the lower sides of left and right fixing apparatus (5, 6) for the introduction and electrophoresis of samples and the chip (2) is pressed while reducing the interval between the left and right fixing apparatus (5, 6). Then, the chip is tightly compressed and fixed to Elastic plate (7) that is layered onto the vertical cut portion of the bottom side, and simultaneously, two non-leaking buffer solution storage tubs are formed.

(2) Preparation for Electrophoresis Channels

Electrophoresis channels (8) that are capillary separation tubes (1) on the chip are filled with a buffer solution for electrophoresis or a medium for separation in advance before they are used. A solution or medium to be filled is filled into one storage tub (3), and a negative pressure is applied to another storage tub so that the solution or medium is sucked into the channels. On the contrary, the channels may be filled by pushing in the solution or media by applying a positive pressure. In order to prevent drying of the material filled in the channels, both storage tubs should be filled with proper solutions immediately after filling.

(3) Capillary Sample Delivery Apparatus

The samples that are subject to electrophoresis are sucked into a tube set for the collection of samples by a negative pressure from a sample container stored in a 96-well-type storage tub, and transferred to the front of each corresponding separation tube. And a small amount (less than 1 μL) of each sample is ejected by a positive pressure. This separation tube set may be loaded onto the sample suction and ejection device of the automatic interval adjustment type described in Korean Patent Application No. 2004-28405 filed by the present applicants (refer to FIG. 4).

(4) Use of a Non-Polar Solvent for the Prevention of Diffusion of Samples

In order to prevent thus ejected samples from being diffused during the process of introduction into the separation tubes, the buffer solution storage tub at the side of the sample introduction port is filled with a non-polar solvent (such as silicon oil, mineral oil, polyolefin oligomer, etc.) in advance. It has been found that proteins or DNAs have not been diffused in the solvent in the storage tub as the time has passed if a non-polar solvent has been used. Such fact has contributed to obtaining remarkable effects of having advantages that it has not been necessary to have sample introduction apparatus such as the conventional complicated cross-shaped paths or individual storage tubs, and the separation of the samples has been done more precisely by blocking problems such as diffusion in each storage tub, etc. from the beginning. FIG. 5 shows an example in which the sample ejected maintains its shape without being diffused even as the time passes by according to the present invention. As shown in FIG. 5, it is seen that the sample ejected is not diffused at all as the time passes by or its shape is not changed, which implies that the separation work may be done very precisely if non-polar solvents of the present invention such as silicon oil, etc. are used.

(5) Electrical Injection of Samples having the End Parts of Sample Ejection Tubes as Electrodes Each sample ejected to the front side of the corresponding separation tube is introduced into the corresponding separation tube by the negative electric field (or positive electric field) applied to the metal part of the end part of each ejection tube (20). A sample is introduced smoothly if the sample ejected is directly in contact with the inlet of the separation tube. FIG. 6 shows the process how samples are introduced. It is clearly seen that a specific sample is not injected into the neighboring separation tubes due to diffusion, etc. during the process of ejection. FIG. 7 is a photograph showing that samples are introduced into the neighboring tubes sequentially. It is seen that the firstly introduced sample is introduced into the separation tube of the sample very accurately without being affected by the introduction of the samples in neighboring separation tubes and without interference.

(6) Automatic Condensation and Electrophoresis of Samples

When electrophoresis is begun by replacing the non-polar solvent with an electrophoresis buffer solution and applying an electric field to a linear electrode attached to a fixing apparatus after samples are introduced into the separation tubes in the method shown in the above (5), as shown in FIG. 8, the sample bands are condensed automatically for the moment, and the separation of the DNA bands by electrophoresis is begun subsequently. FIG. 8 shows that 8 kinds of DNAs mixed are well separated.

(7) Preparation for the Subsequent Electrophoresis

After electrophoresis is completed as described in the above, the buffer solution, polymer medium for separation, non-polar solvent, etc. are changed and filled again for the subsequent DNA analysis. This manipulation is done automatically by pipets moving among each storage container, storage tub, and waste solution storage container of such solution.

(8) Operation of Analytical System

A series of such manipulation is done automatically according to the order prescribed in the program according to hydromechanics and robotics manipulation.

BRIEF DESCRIPTION OF THE DRAWINGS

The accompanying drawings, which are incorporated in and constitute a part of this specification, illustrate the embodiment of the invention and, together with the description, serves to explain the objects, advantages, and principles of the invention.

In the drawings.

DESCRIPTION OF THE DRAWINGS CODE

Figure 1:
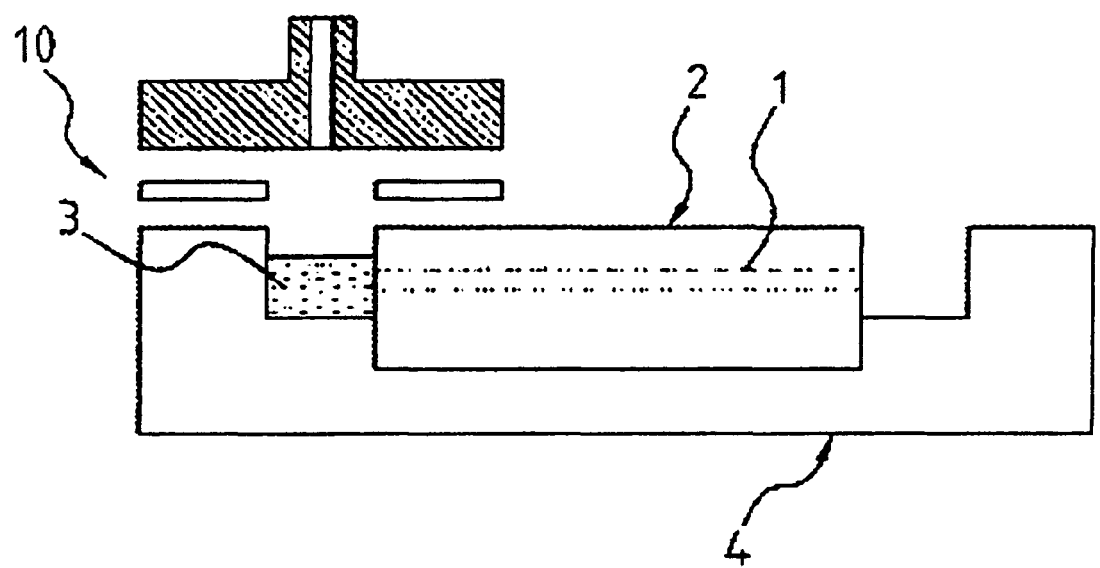
FIG. 1 shows a multi-channel microminiaturized electrophoresis device with individual sample wells omitted according to the present invention.
Figure 2:
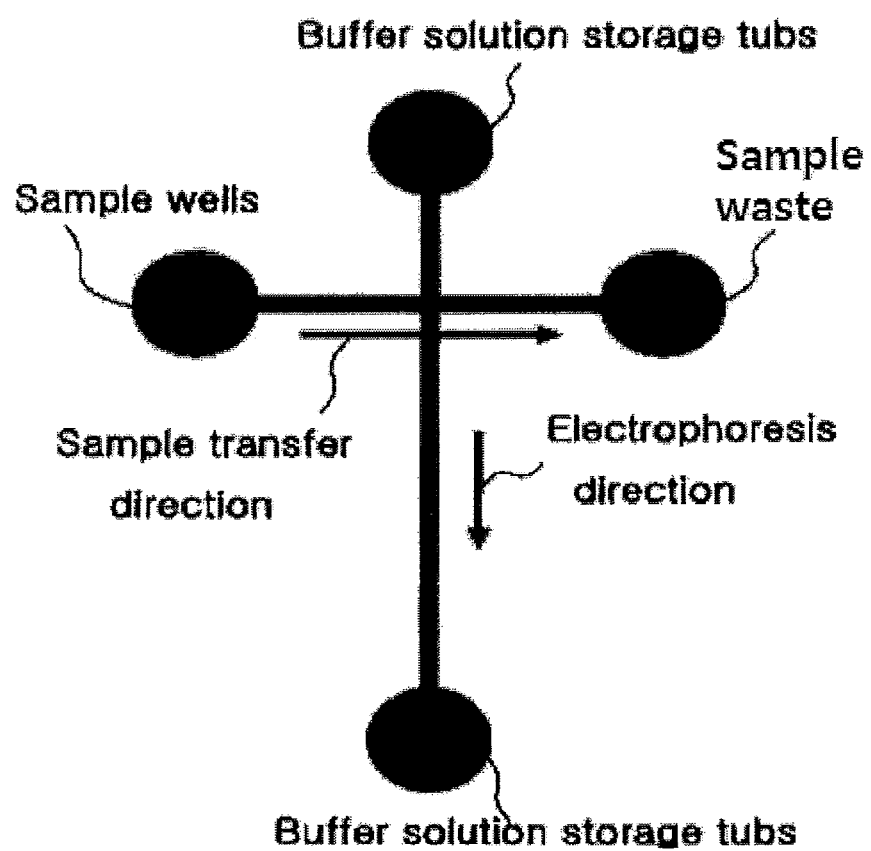
FIG. 2 shows a typical cross-shaped fluid path for the injection of samples that is mounted on an electrophoresis chip equipped with individual sample injection ports and branch tubes for the formation of the cross-shaped fluid path that are required by the conventional technology related to the introduction of samples.
Figure 3:
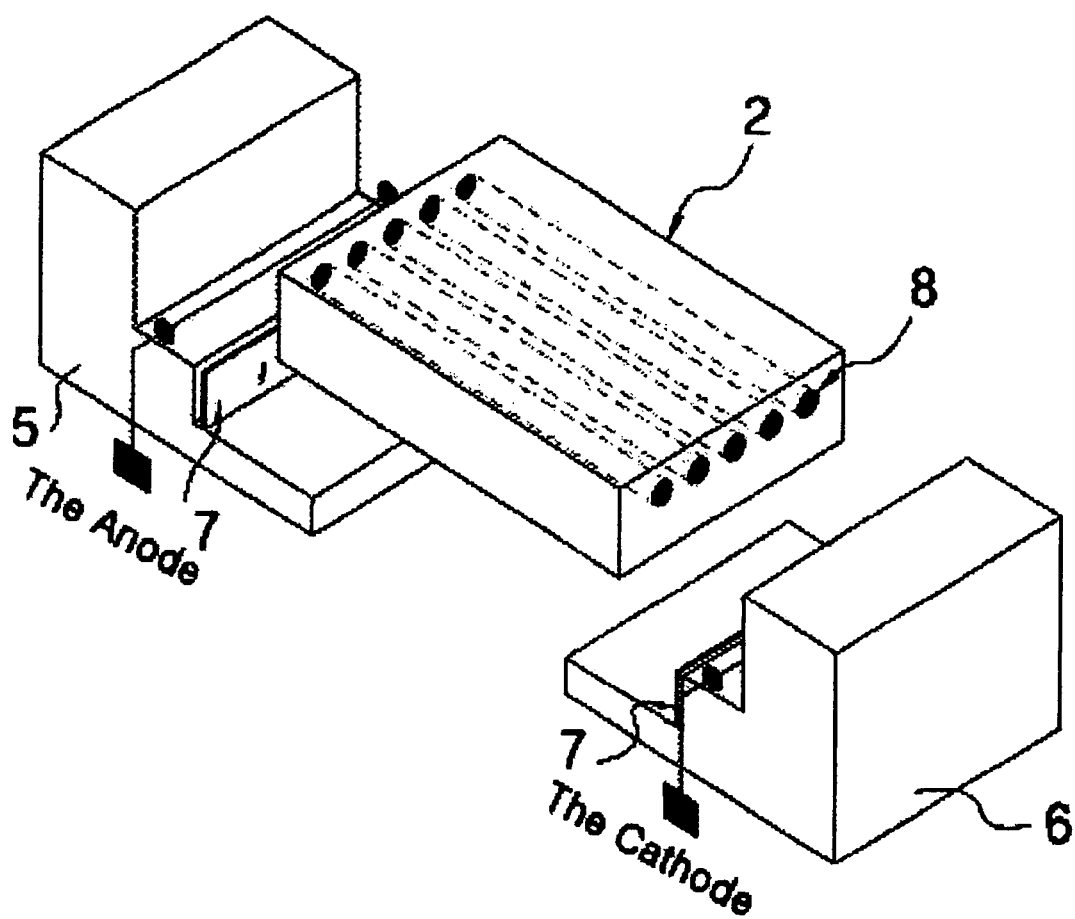
FIG. 3 shows apparatus for fixing the electrophoresis chip according to the present invention.
Figure 4:
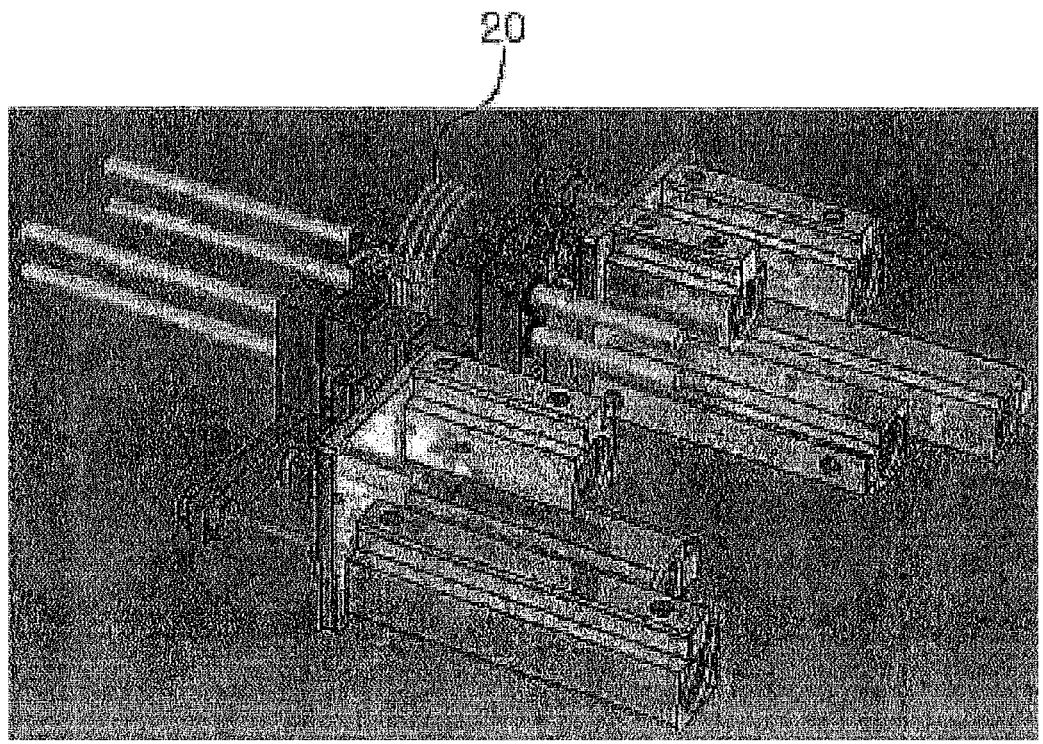
FIG. 4 shows a sample suction and ejection device of the automatic interval adjustment type according to the present invention.
Figure 5:
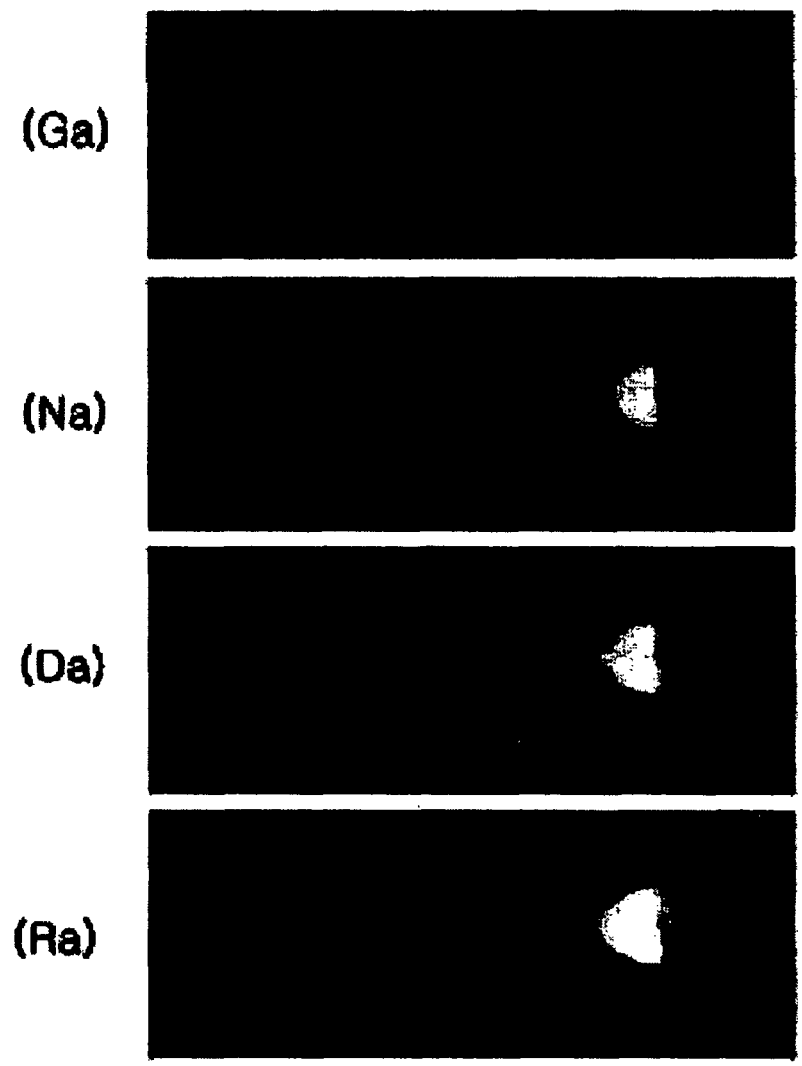
FIG. 5 is a photograph showing that a sample is not diffused or scattered in a non-polar solvent while the sample is ejected.
Figure 6:
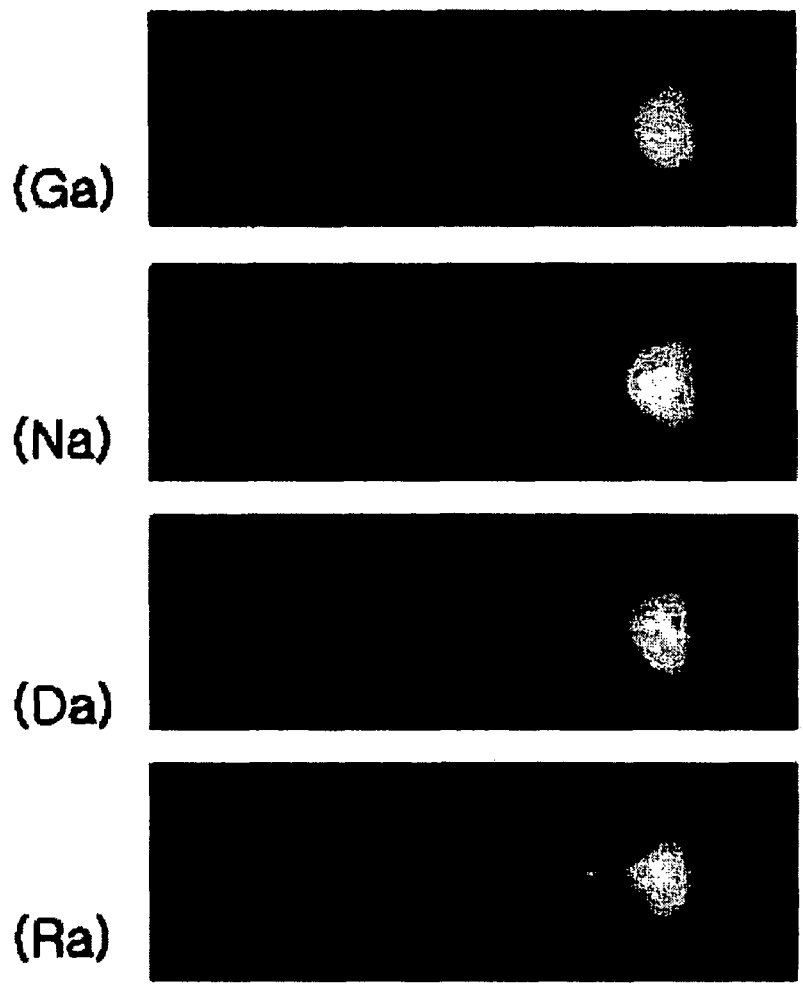
FIG. 6 is a photograph showing the process how a sample is introduced into a separation tube according to the application of an electric field according to the present invention.

1: Capillary separation tube
2: Electrophoresis chip
3: Storage tub
4: Fixing plate
5: Left fixing apparatus
6: Right fixing apparatus
7: Elastic plate(silicon plate)
8: Electrophoresis channel
10: electrophoresis device

DESCRIPTION OF A PREFERRED EMBODIMENT

Injection and Separation of DNA Samples using Multi-Channel Electrophoresis

Feasibility of the above-described methods by applying the following conditions is experimented. An electrophoresis chip is a chip having 24 capillary channels. Capillary channels having an inner diameter of 100 μm and a length of 30 mm are used for the electrophoresis chip. And the channels are filled with 3% polyethylene oxide (PEO, Aldrich Company) in advance.

For the electrophoresis buffer solution, 0.5×TBE buffer (45 mM tris-borate, 1 mM EDTA, pH 8.0) corresponding to a usual buffer solution is used, and a mixed solution of 100, 200, 300, 400, 500, 600, 800, and 1,000 bp DNAs is used for the sample to be separated.

Silicon oil is injected into the storage tub of the electrophoresis device as a non-polar solvent, and the sample is injected into the capillary tubes which are analysis tubes by applying 200 V for 20 seconds to the ends of the ejection tubes of the sample. After the sample is injected, the silicon oil in the storage tub of the electrophoresis device is replaced with a buffer solution, and the sample is separated through electrophoresis by applying a voltage of 200 V. Separated DNAs are mixed with 10× SybrGreen I. DNAs are then separated by detecting DNA bands obtained through photographing the fluorescence obtained by exciting the above mixture with 488 nm of Ar ion laser with a digital camera mounted on a microscope.

Figure 7:
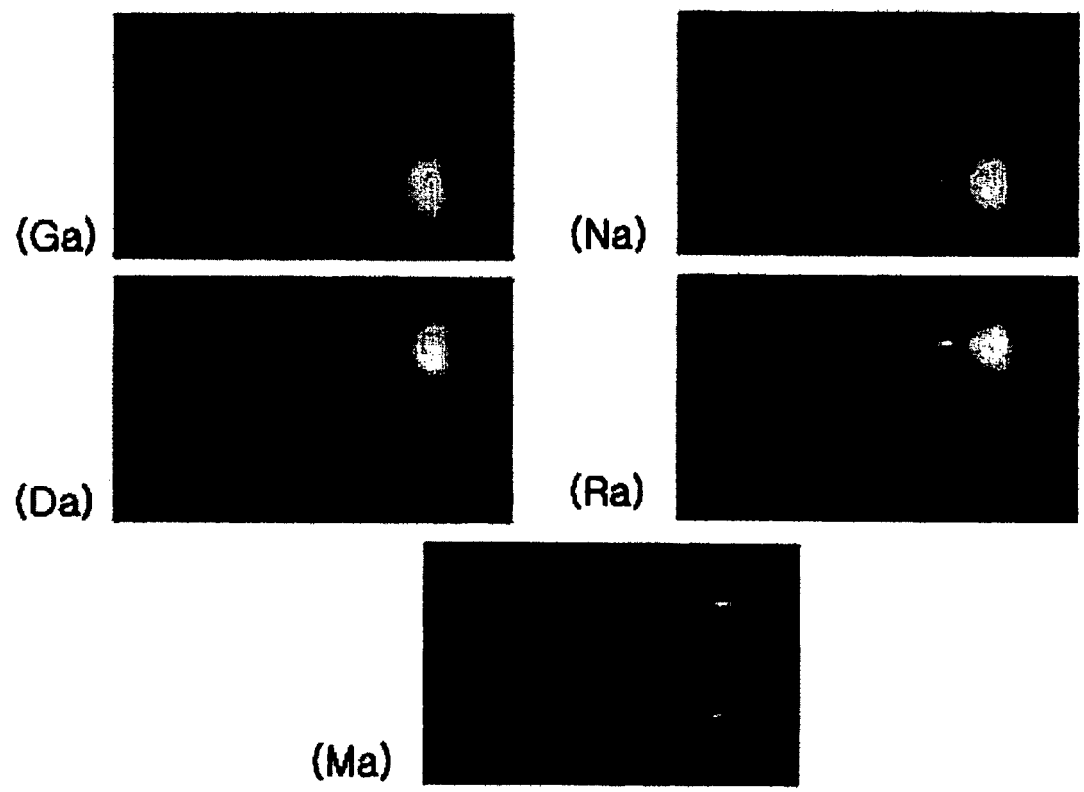
FIG. 7 is a photograph showing that, in the injection of samples according to the present invention, firstly introduced DNA is not affected by the injection of the samples into sequential neighboring separation tubes.
Figure 8:
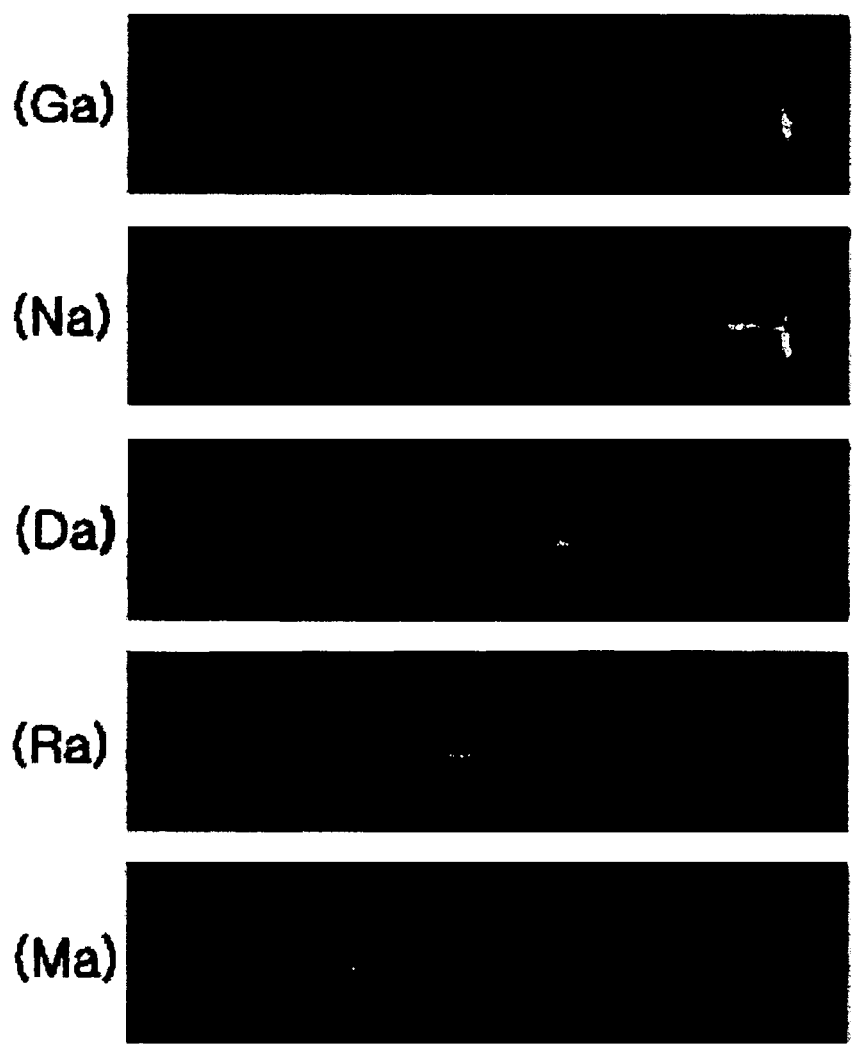
FIG. 8 is a photograph showing that the sample injected into the electric field of the present invention is separated successfully through continuous electrophoresis.

The results are shown in FIGS. 7 and 8. As shown in FIG. 7, a sample is inputted well by sequential inputting without interference by the samples inputted into neighboring separation tubes and without diffusion into separation tubes. And as shown in FIG. 8, it is confirmed that the sample inputted is separated and detected without any difficulty.

INDUSTRIAL APPLICABILITY

The present invention enables simple manufacturing and practical use of a microminiaturized multi-channel electrophoresis device as well as cost reduction in that a multiple number of samples is led to separation tubes without interference due to the diffusion of the samples by injecting the samples into the separation tubes by inputting a non-polar solvent into a buffer storage tub without a need to have a separate sample inputting storage tub corresponding to each separation tube shown in the conventional electrophoresis device.

Further, by removing the conventional individual sample injection ports and branch channels for the injection of samples from the chip structure, it is possible to realize the densification of electrophoresis channels and to expand the scope of application of the gene analytical system based on multi-channel electrophoresis chips through the introduction of the concept of length-variable chips.

Still further, another effect of the present invention is to give some room to setting of the location in the practical use of distance-variable multi-channel sample suction and ejection apparatus of the present invention. That is, since not only the ejected sample is not spread but also it is induced and introduced electrically toward the corresponding separation tube, the sample can be injected accurately even if the relative location of the ejection tube with respect to the location of the separation tube is somewhat out of balance. And such technique of introducing samples is proper for the automatic operation of the system and may assume the function of complete automation of the analytical system on the whole.

While one preferred embodiment of the invention has been shown and described, it is to be distinctly understood that the invention is not limited thereto but may be otherwise variously embodied and practiced within the scope of the following claims:

What is claimed is:

1. A method of separation of chemical substances employing a multi-channel electrophoresis device, characterized by that:
    said multi-channel electrophoresis device is comprised of two pieces of left and right fixing apparatus each having a linear electrode; an electrophoresis chip with 2 or more electrophoresis channels that are capillary separation tubes; and storage tubs that are formed by compressing and fixing said electrophoresis chip by moving said left and right fixing apparatus from both sides; and
    said method of separation of chemical substances includes,
    a step of filling the capillary separation tubes with a buffer solution,
    a step of filling one of the storage tubs, which is at a side of sample introduction, with a non-polar solvent,
    a step of having samples ejected from sample ejection tubes to front sides of the corresponding capillary separation tubes and then having the samples not diffused in the non-polar solvent but injected directly into said capillary separation tubes of said electrophoresis chip by applying a voltage to the metal parts of the end parts of said sample ejection tubes in said one of the storage tubs, and
    a step of replacing the non-polar solvent with an electrophoresis buffer solution and applying an electric field to said linear electrodes,
    wherein said multi-channel electrophoresis device has no individual sample wells.

2. The method of separation of chemical substances employing a multi-channel electrophoresis device of claim 1, characterized by the samples ejected from the sample ejection tubes are in direct contact with inlets of the capillary separation tubes thereby the samples being introduced smoothly into the capillary separation tubes.

3. The method of separation of chemical substances employing a multi-channel electrophoresis device of claim 2, characterized by that one of said storage tub is filled with one non-polar solution selection from silicon oil, mineral oil, and polyolefin oligomer.

4. The method of separation of chemical substances employing a multi-channel electrophoresis device of claim 3, characterized by that said non-polar solvent to be used is silicon oil.

5. The method of separation of chemical substances employing a multi-channel electrophoresis device of any of claims 1 through 4, characterized that said chemical substances are DNAs or proteins.

* * * * *